(12) United States Patent
Lucas

(10) Patent No.: US 6,221,010 B1
(45) Date of Patent: Apr. 24, 2001

(54) HOME MEDICAL SUPERVISION AND MONITORING SYSTEM

(76) Inventor: Donald A. Lucas, 16300 Elm Rd., Maple Grove, MN (US) 55311

( * ) Notice: Subject to any disclaimer, the term of this patent is extended or adjusted under 35 U.S.C. 154(b) by 0 days.

(21) Appl. No.: 09/347,348

(22) Filed: Jul. 2, 1999

(51) Int. Cl.[7] ..................................................... A61B 5/00
(52) U.S. Cl. .............................................................. 600/300
(58) Field of Search ........................ 600/300; 340/573.1; 128/906

(56) References Cited

U.S. PATENT DOCUMENTS

| | | | |
|---|---|---|---|
| 5,440,301 | * | 8/1995 | Evans ............................... 340/870.11 |
| 5,696,492 | * | 12/1997 | Sakamaki et al. ..................... 340/573 |
| 5,785,650 | * | 7/1998 | Akasaka et al. ...................... 600/300 |
| 5,911,132 | * | 6/1999 | Sloane .................................. 600/300 |
| 5,954,641 | * | 9/1999 | Kehr et al. ........................... 600/300 |
| 5,967,975 | * | 10/1999 | Ridgeway ............................. 600/300 |

* cited by examiner

Primary Examiner—Max Hindenburg

(57) ABSTRACT

A home medical supervision and monitoring system with computer-controlled base station provides medical supervision of an individual and controls medical monitoring, environmental, and safety devices. Modular electronic components, a real-time operating system and multilevel application software provide decision-making choices to inform a monitoring service or the like if a medical crisis is occurring or an adverse environmental or safety condition exists.

Subsystems include medical monitoring devices to control and monitor specific medical conditions. If a crisis is detected, predefined physician instructions are implemented. A daily medical supervision subsystem records messages to be played back at preset intervals to supervise the individual's daily medical, safety or environmental activities under control of application software. A personal distress call subsystem can contact a monitoring service by pushing a distress button or by voice activating a communication circuit via a speaker telephone. Safety and environmental sensing devices such as motion, fire, smoke, etc., detect abnormal conditions and notify the base station while an archiving subsystem collects and processes information on a hard drive for later retrieval. The system has an optional medication-dispensing cabinet that will open a compartment at a prescribed time containing prescribed medication.

8 Claims, 6 Drawing Sheets

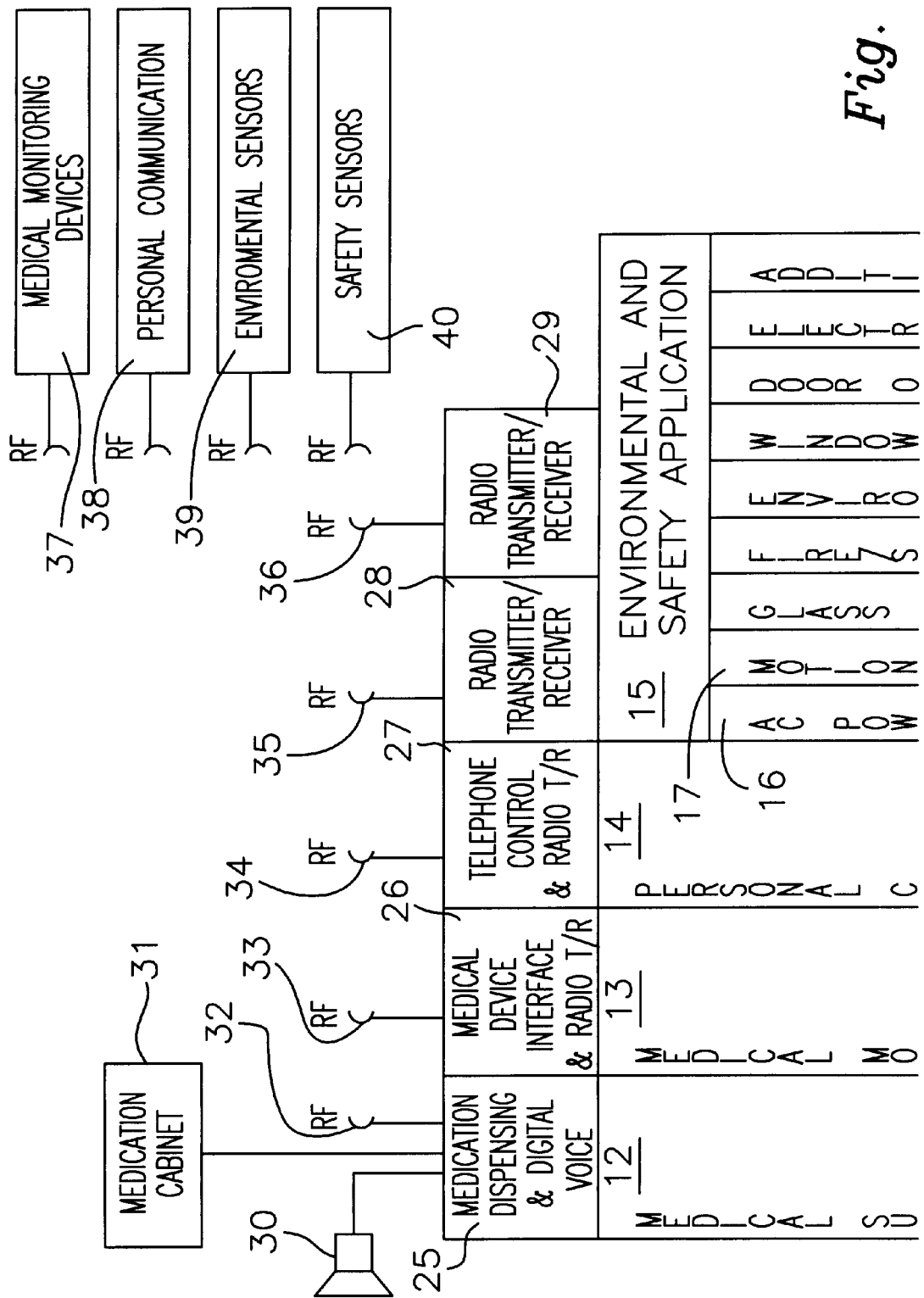

Page 1 …

HOME MEDICAL SUPERVISION AND MONITORING SYSTEM

BACKGROUND OF THE INVENTION

1. Field of the Invention

This invention relates generally to the field of monitoring systems, and more particularly to home medical supervision and monitoring systems.

2. Description of Related Art

The median age of the world's population is aging. Modern medicine and medical techniques have allowed people to live much longer and it is not unusual for individuals to reach the age of 90–100 years of age. Statistics indicate 80 million people in the United States, or 1 in 5, will be categorized as senior citizens by the year 2050. At the same time, the average lifetime work cycle has shortened with people retiring at an earlier age, often as young as 50 or 55 years old. Accordingly, lifetime savings and retirement plans can be exhausted by the time an individual reaches 65 or 70 years of age. When an elder person is no longer able to live independently, the younger generation is often unable or unwilling to take the person into their home and provide necessary care. Therefore, the elderly are often placed into senior citizen care facilities, quickly exhausting their savings and retirement plans. Without sufficient independent funds, state and federal governments often have to pay for the individual's care. Often the decision to place an elderly parent or relative into a long-term care facility follows a health crisis when it is determined that the patient will require medical monitoring and supervision by professional health care personnel. A number of systems have attempted to help the health care recipient in their own home, alleviating the need for personnel-supervised separate heath care facilities.

U.S. Pat. No. 5,440,301 entitled Intelligent Alerting and Locating Communication System uses a hardware implementation of a scanner to detect information by polling remote devices, either hard-wired or over a radio frequency link. The polling sequence transmits an address and only the unit that has the corresponding address responds, returning the "normal/abnormal" status of that particular sensing device. The information is returned to a hardware computer controller. The software running in a personal computer can retrieve this information and uses this information to generate a display showing the location of the sensors or detectors having abnormal states.

U.S. Pat. No. 5,291,191 entitled Medicine Dispenser is a selfcontained device with a number of drawers that contain medication to be taken at predefined times as monitored by a clock. The drawer opens at the given time and a sound mechanism broadcasts an audible description of the medication.

U.S. Pat. No. 5,696,492 is to a medical alarming system that delivers an alarm to a nurse in response to an abnormal change occurring during the monitoring of physiological signals of a person confined to bed in a hospital or at home. A video camera provides the nurse at a nursing station with a view of the individual if and when an alarm occurs. The system is equipped with three devices to get the attention of the nurse or attendant: a physical display; a speaker for an audible alarm; and a signal sent to a pager.

SUMMARY OF THE INVENTION

An advantage of the present invention is to provide a medical supervision and monitoring system to help individuals needing health care to remain in their home surroundings and enhance their independence of personnel-intensive care.

A related advantage of the present invention is to provide a medical supervision and monitoring system to allow individuals needing health care to remain in their home surroundings while receiving necessary medical monitoring, supervision, and care.

Another advantage of the present invention is to provide a medical supervision and monitoring system that is reliable, yet flexible.

Yet another advantage of the present invention is to provide a medical supervision and monitoring system that takes greater advantage of software control in order to keep failure to a minimum.

In accordance with an embodiment of the invention, a medical supervision and monitoring system for individual patients comprises a medical monitoring system to monitor at least one medical condition of a patient that is operatively connected to a computer control means; an environmental sensing system having at least one sensor to detect at least one condition selected from the group consisting of: power, motion, fire, smoke, carbon monoxide, window and door, said detector in operative communication with the computer control means; and a computer based system having computer control means operatively connected to the medical monitoring system and the environmental sensing system to detect abnormal states and transmit a responsive action dependent thereon.

BRIEF DESCRIPTION OF THE DRAWINGS

Other advantages of the present invention will become apparent from the following descriptions, taken in connection with the accompanying drawings, wherein, by way of illustration and example, an embodiment of the present invention is disclosed.

DETAILED DESCRIPTION OF THE PREFERRED EMBODIMENT

Figure 1B:
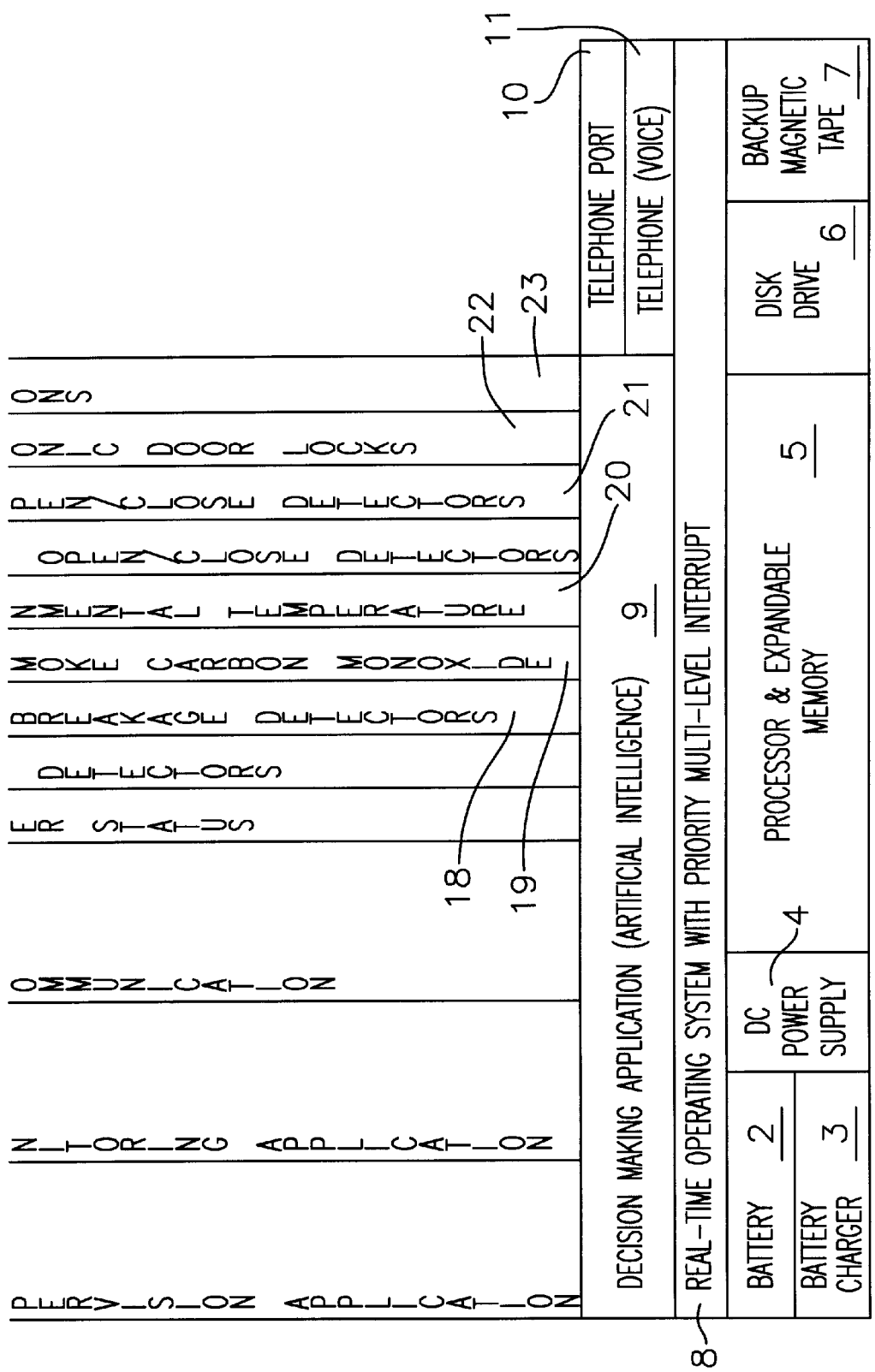
FIG. 1 is a block diagram of the system according to a preferred embodiment of the invention.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

In accordance with important features of the preferred embodiment of the present invention, a home medical supervision and monitoring system includes a computer-controlled base station that provides medical supervision of an individual while controlling a number of medical monitoring, environmental, and safety devices. The system has modular electronic components, a real-time operating system and multi-level application software that provide artificial intelligence type decision-making capabilities. In this way, the software and modular hardware are easily modifiable and upgradable for a variety of applications. Under appropriate circumstances, the computer controlled means can inform a remote location at which a monitoring service, physician, family member or caregiver may be present that a crisis is occurring with the individual or an adverse environmental or safety condition exists within the premises of the monitored individual. In the illustrated embodiment, the base station is a self-contained mechanical package housing a processor and expandable memory, a hard disk drive, a magnetic backup tape and mechanical packaging for plugable modules which provide additional variable capabilities. A DC power supply that obtains its power from a storage battery kept charged via an AC-powered battery charger powers the system. The system derives its functionality and intelligence from modular application software that is executed under control of a real-time computer controlled operating system. The real-time operating software has a master scheduler for control of the task-specific applications dealing with the individual's physiological and environmental needs and determines what application module is executed and for how long the selected module retains control before transferring control to another module. In certain circumstance, multiple modules may have simultaneous control. The real-time operating software also has a priority multi-level interrupting module that can process external hardware interrupts indicating a higher priority than is currently assigned by the scheduler.

The medical monitoring and supervision system according to the preferred embodiment of the present invention is an integrated system that, for illustration and discussion purposes may be separated into six subsystems, all being regulated by computer control. In no particular order, each subsystem is discussed in detail below, though through computer control any one subsystem or a combination of subsystems may simultaneously perform supervision, control or otherwise.

Medical monitoring subsystem 13 can transmit commands or receive continuous real-time data via a radio transmitter/receiver 33. A remote monitoring device 37 can be implanted or worn by the individual for a specific medical condition. Some examples of such devices include an implanted pacemaker, implanted cardioverter defibrillator and portable cardiac monitor like an electrocardiogram (ECG). The medical monitoring software will continuously process incoming data, testing for a specific set of parameters as defined by the attending physician. The real-time operating decision-making software is called to take the appropriate action as defined by the doctor or caregiver whenever the medical-monitoring subsystem or application 13 has detected a parameter, defined by the attending physician, or when the signal is lost between the base station and the monitored patient. The incoming data is also sent at a predetermined interval time to an archiving file and stored on the hard drive. A doctor or hospital can retrieve this archived medical data at any time. The individual assessing the information may be required to give a security check and code. A second or even a third medical monitoring application can be added with additional software modules and radio interfaces.

Medical supervision subsystem or application 12 includes a voice announcing device 25, operably connected to output device 30 where the voice of a family member, a physician or caregiver is digitized and stored on an associated storage medium such as a hard drive to be retrieved by the application software when specific commands or directions are to be given to the monitored individual patient. Individual messages can be removed or new ones added though in person or remote means by the local communications devices or through the telephone. A security system may again be employed to ensure only authorized access.

The personal communication software 14 monitors a personal communication device 38 worn by the individual patient through radio transmitter/receiver 27, 34 that performs one of two functions. Transmitter/receiver 27 will receive a distress signal from the individual, which causes the application software to call the decision-making software to activate the predefined crisis intervention for the individual's distress signal. The application software can call the decision-making software to establish a speaker telephone communication with a monitoring service, doctor, or caregiver. An example of a personal communication unit 38 is a small unit worn around the neck or pinned or clipped onto the individual that has a radio frequency transmitter and a button. Pushing the button causes a distress signal to be sent to the base station via rf 34. The base station then dials the monitoring service or the caregiver to inform them that a distress signal has been received from this individual.

Another example of the personal communication device 38 is also worn around the neck, pinned or clipped onto the individual. It has a button, which activates a telephone call to the caregiver or a monitoring service through appropriate telephone interconnections through telephones (voice) 11. This model has a small microphone and speaker system so that the person can talk wherever they are. For example, if an individual sat down but could not get up or has gone to the bathroom but cannot get up or leave the facility for any number of reasons such as loss of strength, feeling faint, stroke, disoriented, etc he or she may initiate telecommunication to the outside.

Environmental and safety subsystem collects data from a number of remote detectors and/or sensing devices. The sensors may sense a variety of environmental and safety devices such as the AC power supply status 16, a variety of strategically placed motion detectors 17, glass or window breakage detectors 18, fire, smoke and carbon monoxide detectors, depicted collectively as 19, environmental temperature readings 20, windows open/close detectors 21, doors open/close detectors 22, and electronic door lock status detectors 23. Additional detectors may be added to the system through computer control at 24. Environmental and safety subsystem 15 communicates with the remote detectors and/or sensors by write/read addressable hardware registers. When the environmental and safety subsystem sends a command to a remote detector or sensor, it writes a fixed address block, a command block and sets a transmit flag. The address and command is then serialized and broadcast via transmitter 28 and rf 35. The sensors 39 and 40 having the particular associated address will compare the received signal and execute an appropriate command under control by computer or otherwise. When the remote sensor detectors 39 and 40 have executed the command, it will transmit its address and the response to the command back to the computer control base station. Through radio frequency (RF), interface 28, 35, receiving the information will set an interrupt flag to the interrupt handler indicating that a response has been received. Environmental and safety subsystem 15 is then called which in turn reads the address field and the command response. This information is put into the mailbox of the command-issuing subcomponent 16–24. The software will then test for a normal/abnormal state by comparing the received information from the sensors, for example temperature sensor 20. If an abnormal state is detected, the environmental and safety subsystem 15 will call the decision-making software, which will take predetermined corrective action.

For one example of how the environmental subsystem is employed, the environmental and safety software may be programmed to call the decision-making software if the temperature of the living quarters drops 10 degrees. In this example, the thermostat is set of 68 degrees and the temperature has dropped to 58 degrees, so the decision-making software is called. The decision-making software goes immediately to the stored physical profile of the monitored individual to retrieve information about the individual. In this instance, her name is Mary, she is 67 years old and lives alone in Minneapolis, Minn. Because of the reported low temperature, the decision-making software goes to the real-time operating system to determine the time and the date, which is 3:00 P.M. on January 7. With this information and the physical profile data, it indicates that it should be very cold at this time in Minnesota. It also checks the archive file to see whether or not an incident like this has happened before and how long ago it was. If the archive has no history of a similar incident, the decision-making software determines that it must then scan the environmental and safety subsystems to determine what detectors and sensors are available to it that would help find the cause for the temperature drop. Some possible sources could be the loss of AC power in the living quarters, a furnace not operating correctly, or windows or doors that are not properly closed or sealed.

The decision-making software makes call routines to all the sensors previously listed that apply to this situation. It sends these four calls to the scheduler to immediately test the "normal/abnormal" state of each. When the environmental and safety software tests the front door, for example, it may be discovered unlocked and open. The environmental and safety software reports this to the decision-making software. It then goes to the predefined message routine to see whether or not there was a voice message from a family member or caregiver directing Mary to close and lock the front door. If it found a message asking Mary to close and lock the door, the message is broadcast. Then the decision-making software sends a request to the scheduler to keep monitoring the front door until it is closed and locked. This is defined for a period of time. If it is not closed within, for example, 5 minutes, the decision-making software goes to the predetermined action items list to determine whom to call if that action does not occur. It may be determined that it should call a specific family member at work if the door is not closed and locked within five minutes. The decision-making software will continue to monitor the call to be certain it is answered at this number. If no one answers this number, it returns to the predetermined action list of see what the next number is to call or what action should take place until the situation is resolved.

Figure 2:
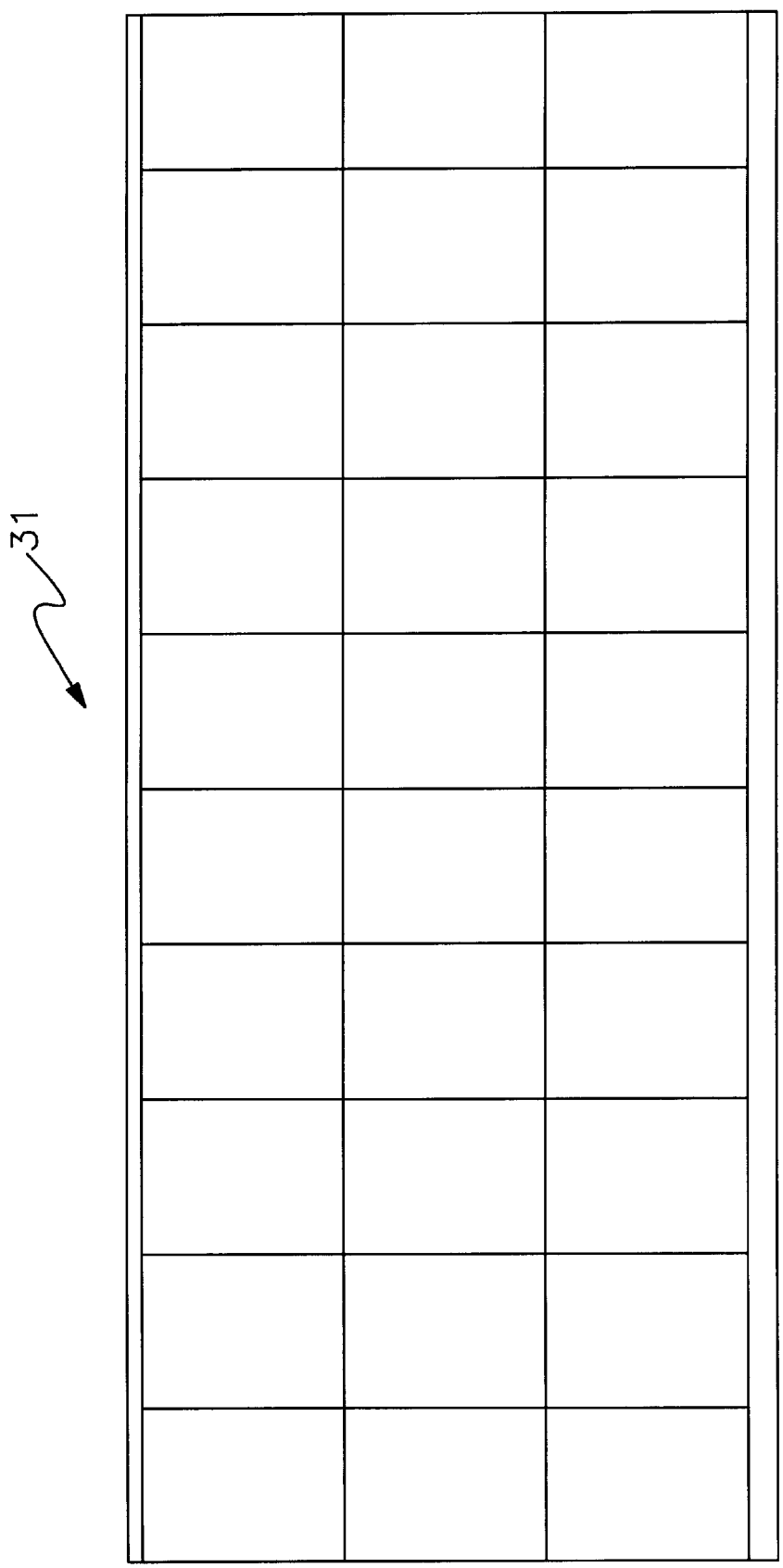
FIG. 2 shows the front of a medication dispensing cabinet containing a number of medication storage compartments in accordance with the invention.
Figure 3A:
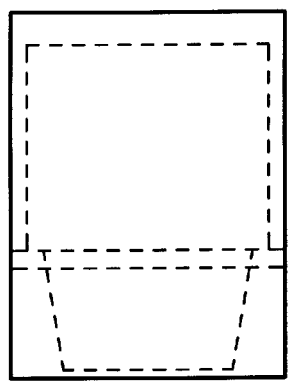
FIG. 3 shows one compartment of a medication dispensing cabinet in the open position and one in the closed position in accordance with the present invention.
Figure 3B:
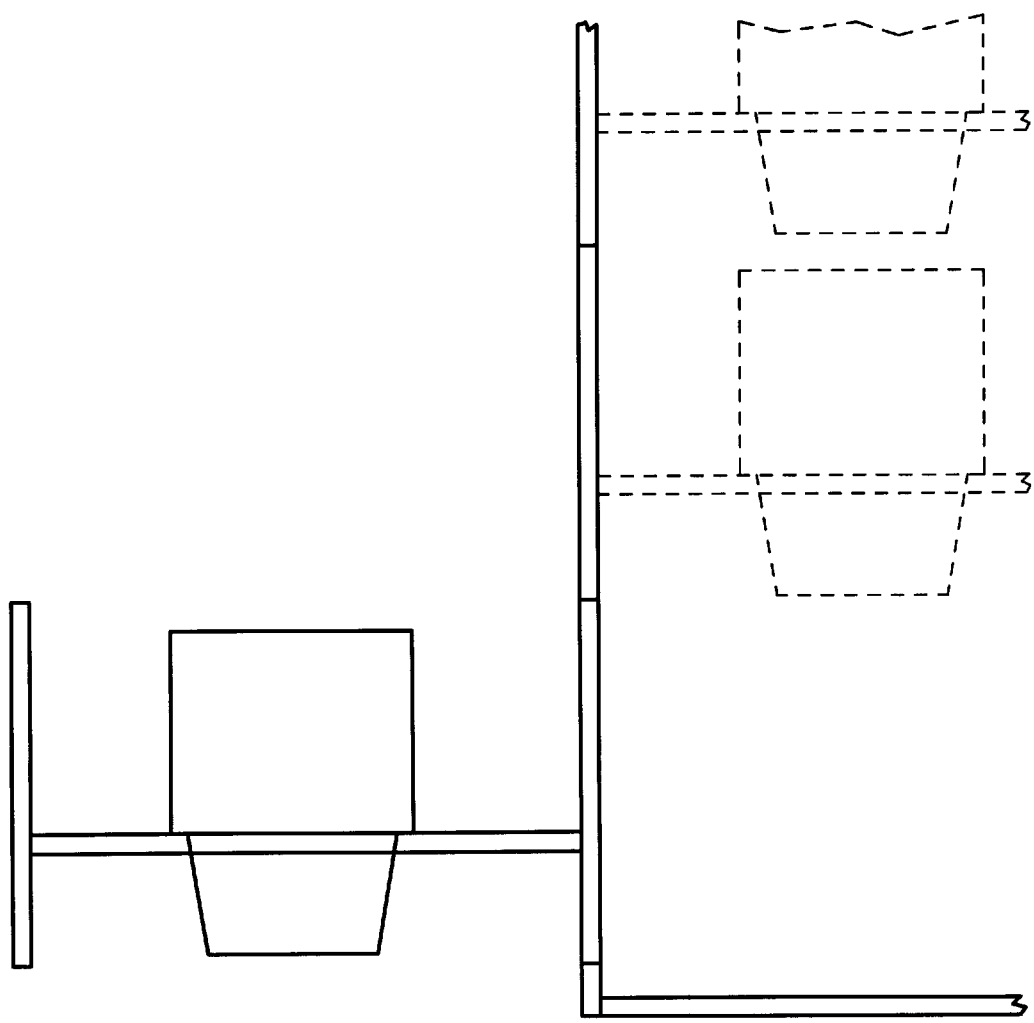

Medication-dispensing cabinet 31 is a generally self-contained package with a number of open-sided trays containing removable cups. Turning briefly to FIGS. 2 and 3, there is show at FIG. 2 a front view of the medication-dispensing cabinet 31 having a plurality of drawers, one each for a time to take medication in the preferred embodiment. Each drawer can open and close according to software computer control in accordance with the programming of the individual situational needs. The cups contain a predefined dosage of medication. When the predetermined time and conditions to dispense medication for the individual patient has been determined by the medical-supervision subsystem 12, one of the medication compartments 31 will open.

The compartment allows easy access for an individual to retrieve medication, even with arthritic hands. Medication-dispensing cabinet 31 may also work in conjunction with the voice communication system 25, 30 to broadcast a digitized voice of a family member, physician or caregiver. This message will be directed to the individual by name, instructing the patient to take the named medication.

When the individual has taken the medication, they will push the compartment closed, which in turn activates a signal to the computer controlled medical-supervision subsystem 12 indicating the medicine has been retrieved and taken. The software records the results of this event for further processing in the archiving subsystem 6, 7, discussed in more detail above. If the individual fails to retrieve the medication within the predefined amount of variable time, the computer controlled decision-making software is called to activate the appropriate predetermined crisis response action as directed by the attending physician and/or caregiver. Medication-dispensing cabinet 31 is a separate unit connected to the computer-controlled base station.

FIG. 3 shows one of the compartments in the open position and one in the closed position. One individual compartment consists of a tray with a secured front that is opened automatically under control of the Medical Supervision Software. The tray has a hole cut in the bottom for placement of a removable cup that will contain the individual's medication to be taken at a preset time. The base of the cup is tapered and weighted to provide stability and easy insertion. When the individual removes the cup to take the medication and places the cup on the table, the cup will not tip over due to a weighted base. And, when it is time to replace the cup into the compartment, the tapered unit makes insertion into the hole easy. The weighted base causes it to settle back into its normal position. When the individual closes the compartment, it signals the Medical Supervision Software that the individual has retrieved the medication. It may also be desirable to have sensors that determine if the medicine has been removed from the cup after replacement in the compartment. The top of the unit contains a telephone keypad that is used by the individual responsible for loading the Medication Cabinet. Access to the cabinet's individual compartments is gained by using the keypad to enter the security code.

Archival subsystem 6, 7 polls the computer controlled decision-making software and all other subsystems at predetermined intervals and stores the information from the subsystems. At the polling time, comparison and analysis may be performed, or delayed until later. The archived information may be stored on any suitable medium such as a hard drive 6 or magnetic tape 7. The information may at an appropriate time be sent remotely, or accessed in-person, by authorized personnel to modify a patient's care profile in the computer controlled decision making software.

The computer-controlled decision-making software provides its input depending on the various activities occurring at any particular time. The Decision-Making Software is, therefore, an artificial intelligence-type computer control of the present medical supervision and monitoring system. The decision-making software has a table of telephone numbers and a series of actions to implement for each possible crisis scenario, which may include a medical crisis as detected by the medical monitoring, failure to retrieve medication(s), a loss of AC power, a fire in the residence or any dangerous residential variable. In this respect, the decision-making software does more than make a telephone call to report a crisis, but can also offer additional assistance and input to the emergency response by retrieving the medical history of the individual from the archival subsystem and sending it via telephone to the attending physician, hospital emergency room and/or ambulance team. The system can electronically unlock the residence door through accessing the environmental and safety subsystem 15, allowing immediate access by the responding emergency team. The decision-making software can also track the day-to-day activity of the individual, thus putting together a lifestyle picture of the individual that may be used to modify the monitoring and supervision, as well as environmental control of the individual. If the decision-making software by using computer control and artificial intelligence-type programming detects any significant behavioral or physiological change within a short time, it can flag or warn the family/caregiver that some intervention may be required. The medical supervision and monitoring system in accordance with the illustrated embodiment is in this effect an electronic, live-in nurse that watches over an individual's medical, environmental and safety factors and it will summon help when a crisis is imminent or is occurring.

The following is a functional example of how a system in accordance with the present invention provides medical monitoring of an individual who has an implanted pacemaker or an automatic implanted cardiovascular defibrillator through the use of its decision making software and subsystems. An implantable pacemaker and implantable cardiovascular defibrillator are currently available from Guidant or Medtronics Corporation.

Appropriate parameters are set and defined by a physician or other caregiver from data collected from the pacemaker or CV defibrillator. When a medical crisis, as defined by the above set criteria occurs with an individual while monitored in his home the current system will follow the directions of the physician, that, for example, specific emergency medication(s) will be dispensed to stabilize the individual. The current invention can send a signal through its RF interface to a, for example, product from ALZA Corp. called E-TRANS™ which can dispense medication electronically through the skin of the patient.

If this medical crisis requires that the patient be transported to a hospital as determined by the doctor, the decision-making software can direct to contact a medical monitoring service through the telephone interface. The system sends coded information which 1) provides the identity of the individual, 2) defines the state of the crisis, 3) what medications have been delivered, and 4) activates a specific medical alert plan as predefined by the physician or other caregiver. The system through its digital voice communication system may broadcast a prerecorded message from a family member or caregiver to inform the patient of the medical crisis and that medical care or intervention is on the way. To prepare for the arrival of the emergency medical care, the system may electronically unlock the door to allow access to the residence by emergency personnel such as police officers and the emergency medical service personnel by the control of the environmental monitor and control subsystem.

In accordance with the preferred embodiment, the instant invention will continue to monitor the activities of the living quarters through, for example, its motion detectors. When the system determines that all activity has ceased therein by monitor of the environmental detectors such as motion detectors, it relocks the door to secure the facility. The system may then go into a security mode while everyone is away and waits to receive a call from the physician or the hospital to provide additional patient medical history file information that may be archived in the storage and archival subsystem to facilitate diagnosis and further treatment.

To further illustrate an example of the system according to a preferred embodiment of the present invention, FIG. 4 shows the flow of decision-making and subsystem monitoring and control for an illustrated situation. At block 41 a scheduler or task management for the microprocessor is illustrated. The medical monitoring application of block 42 is a software module for each medical device the system is monitoring that runs under control of the scheduler 41. In the described example, the medical device is an implanted pacemaker and the software module at block 43 checks the medical device status and retrieves stored data from the implanted pacemaker through its RF interface.

The implanted pacemaker interface of 44 is a radio interface from the manufacturer of the pacemaker that can receive commands from the present inventive system or transmit data back. This interface also has a medical device interrupt that it can send to the system if it determines that the patient's heart is not responding properly to the pacemaker signals. Pacemaker Database block 45 is the memory contained within the pacemaker that holds real-time medical history relating to the heart's action, while Medical Device Interrupt at block 46 is an RF interface of the system that receives the priority medical device interrupt.

External Hardware Interrupt of block 47 is a monitoring application software module that can override the scheduler 41 and call the medical monitoring software, if needed, as determined for input by the medical device. Software module 48, to process the data from the pacemaker, takes the data from whichever manufacturer is used, converts it to the system's format, time-stamps it and synchronizes it to the real-time clock of system, while the file manager software for the medical monitoring device stores the processed data at block 49.

Block 50 illustrates the beginning of the flow of data and control when a medical crisis is detected. Software module 50 takes the processed data from the pacemaker and compares it to the parameters indicated by the physician that have been programmed into the home medical supervision and monitoring system of the present invention. Module 50 uses archived data to determine changes in heart function characteristics and processes the data from the pacemaker when it generates a medical device interrupt indicating it has detected a medical problem with the patient as defined by the manufacturer's parameters. When module 50 detects a medical problem or a medical crisis, it calls the decision-making software for appropriate action as programmed in to the system. As the archived information is available and the physician or caregiver is expected to review the information on a regular basis, the information provides a basis to modify the programming to the individual patient and any changes in the patient's routine or care.

Decision Making Software of block 51 is the intelligence that acts as defined by the physician or the family to respond to a medical crisis and interfaces and controls the subsystems, responding as programmed to the variety of situations detected.

Continuing with the example of the pacemaker, in the event of a medical crisis being detected, pacemaker software of block 52 begins a number of tests as determined by the crisis information detected from the pacemaker as to what action to take. For example, at block 53, medication is determined to be given, which may be determined in the affirmative or negative. If medication is to be given, at block 54 a signal is sent to the Electronic Medication Dispensing Unit that might, for example, send a radio signal through its RF interface to a product from ALZA Corporation. Block 55 depicts an ALZA E-TRANS™ electronic device manufactured by ALZA Corporation that dispenses medication electronically through the skin of a patient. In the event no medication is to be given, block 56 under program control determines if an ambulance is to be called, another affirmative or negative decision.

If an ambulance is to be called, a Monitoring Service is contacted, represented by block 57 and at block 58 software sends the ID code, crisis level, and action plan to implement as predetermined by the physician and caregiver. Thereafter, at block 59, a monitoring service can call the ambulance and provide information such as the purpose, what medication the patient is taking, what medication the patient may have received as a result of the crisis through automatic dispensing unit, and directions to the patient's residence.

In anticipation of the help arriving, the system at block 60 can unlock the door to the patient's residence, allowing emergency personnel to gain immediate access during a crisis. In the event the software determines to not call an ambulance, the software proceeds to block 61 and on to block 62. The software depicted at block 62 may call the physician or caregiver with the name and ID code of the patient and notify with the type of crisis and what medication the patient has or has not been given. Archived information form the pacemaker is available at block 63 as requested by the caregiver, monitoring service, or emergency personnel.

The system will monitor and at block 64 check to see if the patient is moving around the living quarters. Software module 64 uses motion detectors in the unit to determine if the patient is moving, or has fallen and is lying somewhere, unable to get up. If the patient is moving about, block 65 may use a digital voice recording to give a message to the patient from a family member or caregiver directing the patient to lie down, as they are having a medical problem. The voice may also reassure the patient that medical assistance has been called or is on the way. If the patient is not moving, the system at block 66 uses a digitized voice system with a message from a family member or caregiver telling the patient to stay where they are and remain quiet and calm. The voice may also reassure the patient that medical assistance has been called or is on the way to help.

A follow-up message is announced if needed at block 67 such as "If you feel you need immediate emergency medical assistance, push the Call Button to notify the Monitoring Service to send emergency medical help." In the event the call button 68 has been activated on the personal communicator device, it calls the monitoring service software. If the call button has not been activated, the system transfers control to the Timer and Pass Counting software at 69 that times the interval between the call for help and the doctor's or caregiver's has answering the call. The timer and pass counting software 69 also will detect when a predetermined amount of time has lapsed indicating it is time to call again for help. In the event no response is detected in the given time interval, software at block 70 recalls the doctor or caregiver and at block 71, software waits for the expected responsive call from the doctor or caregiver.

At block 72 the resolution of the medical crisis is detected and control returns to the scheduler 41.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A medical supervision and monitoring system comprising:
    a medical monitoring system to monitor at least one medical condition of a patient operatively connected to a computer control;
    an environmental sensing system having sensors to detect at least one from the following group: power, motion, fire, smoke, carbon monoxide, window and door, said detector in operative communication with said computer control; and
    a computer based decision making system operatively connected to the medical monitoring system and the environmental sensing system to transmit one or more responsive actions dependent thereon.

2. A medical supervision and monitoring system as claimed in claim 1 further comprising:
    a personal distress monitoring system to contact help by remote means.

3. A medical supervision and monitoring system as claimed in claim 1 further comprising:
    a archiving system to retain information monitored for retrieval at a later time.

4. A medical supervision and monitoring system as claimed in claim 1 further comprising:
    a medication dispensing system that allows access to predetermined medication at predetermined times.

5. A medical supervision and monitoring system as claimed in claim 4 wherein the medication dispensing system includes an indicator indicative of whether the medication has been dispensed.

6. A medical supervision and monitoring system as claimed in claim 1 wherein the responsive action is sending a signal to a remote location.

7. A medical supervision and monitoring system as claimed in claim 1 wherein the responsive action is sending a signal to a speaker for audible reception by the patient.

8. A medical supervision and monitoring system as claimed in claim 1 wherein the responsive action is sending at least one corrective signal to an environmental control device.

\* \* \* \* \*

UNITED STATES PATENT AND TRADEMARK OFFICE
CERTIFICATE OF CORRECTION

PATENT NO. : 6,221,010 B1
DATED : April 24, 2001
INVENTOR(S) : Donald A. Lucas

Figure 4A:
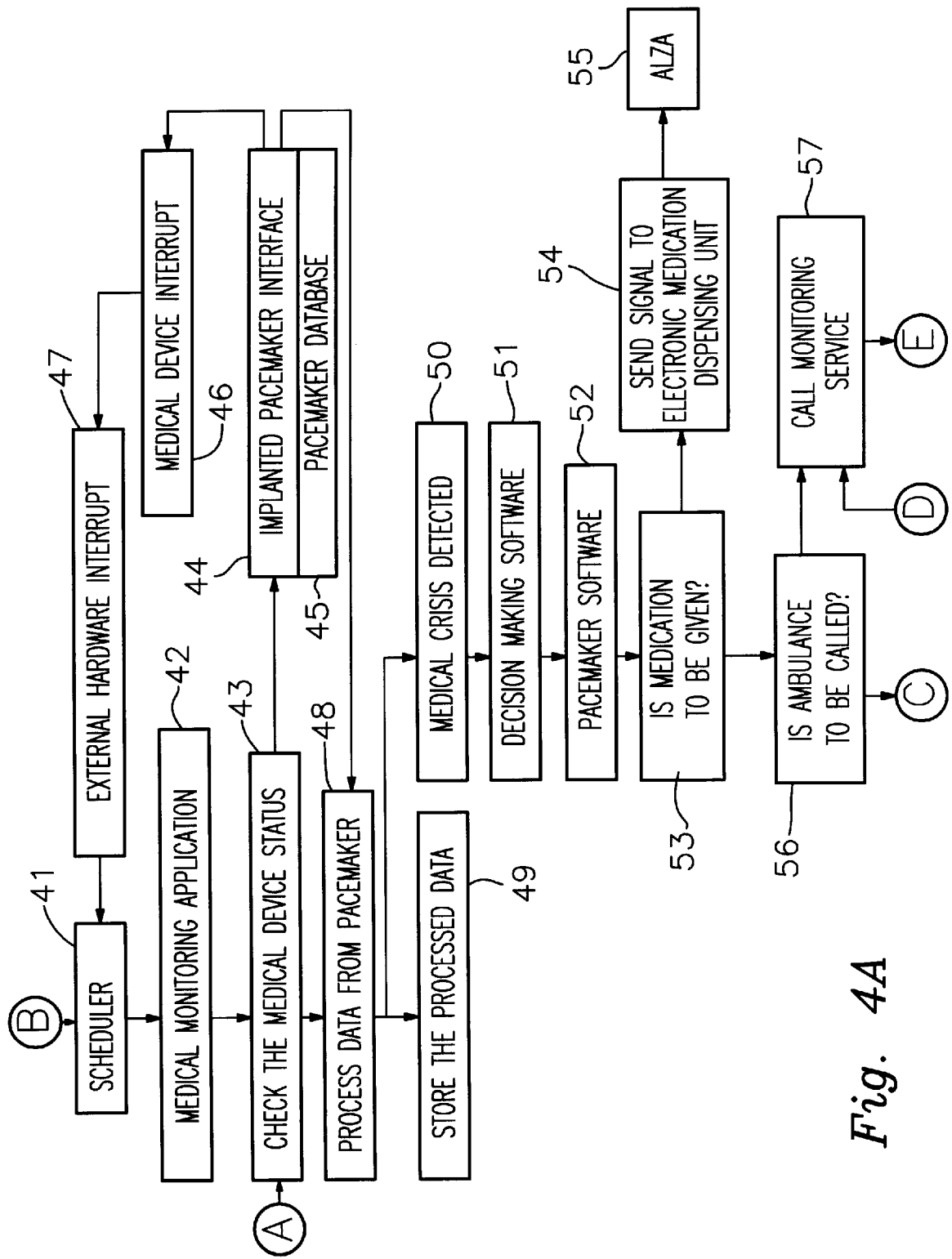
FIG. 4 is a software flow diagram of an example of how a medical supervision and monitoring system in accordance with an embodiment of the invention may be employed.
Figure 4B:
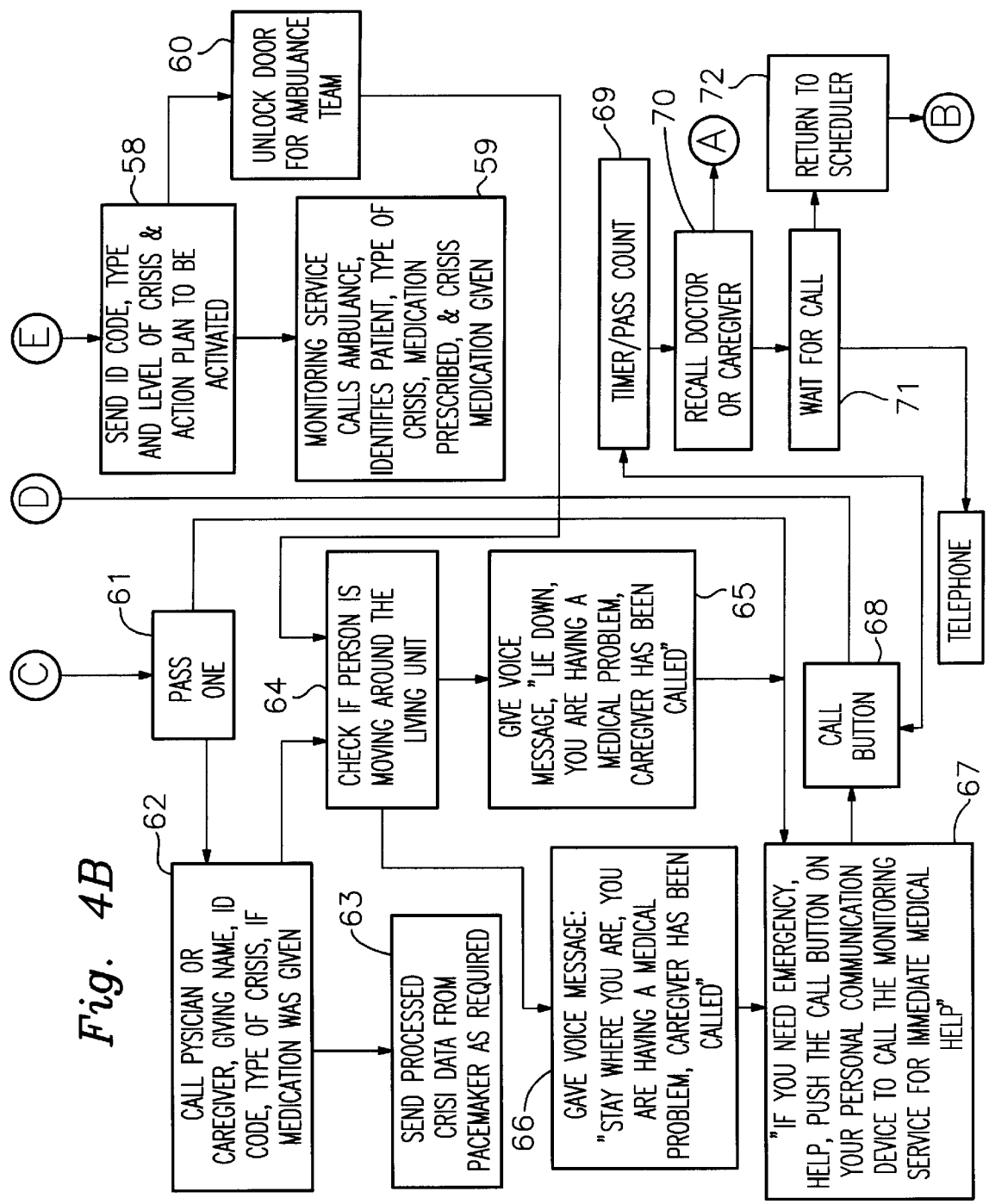
Figure 1B:
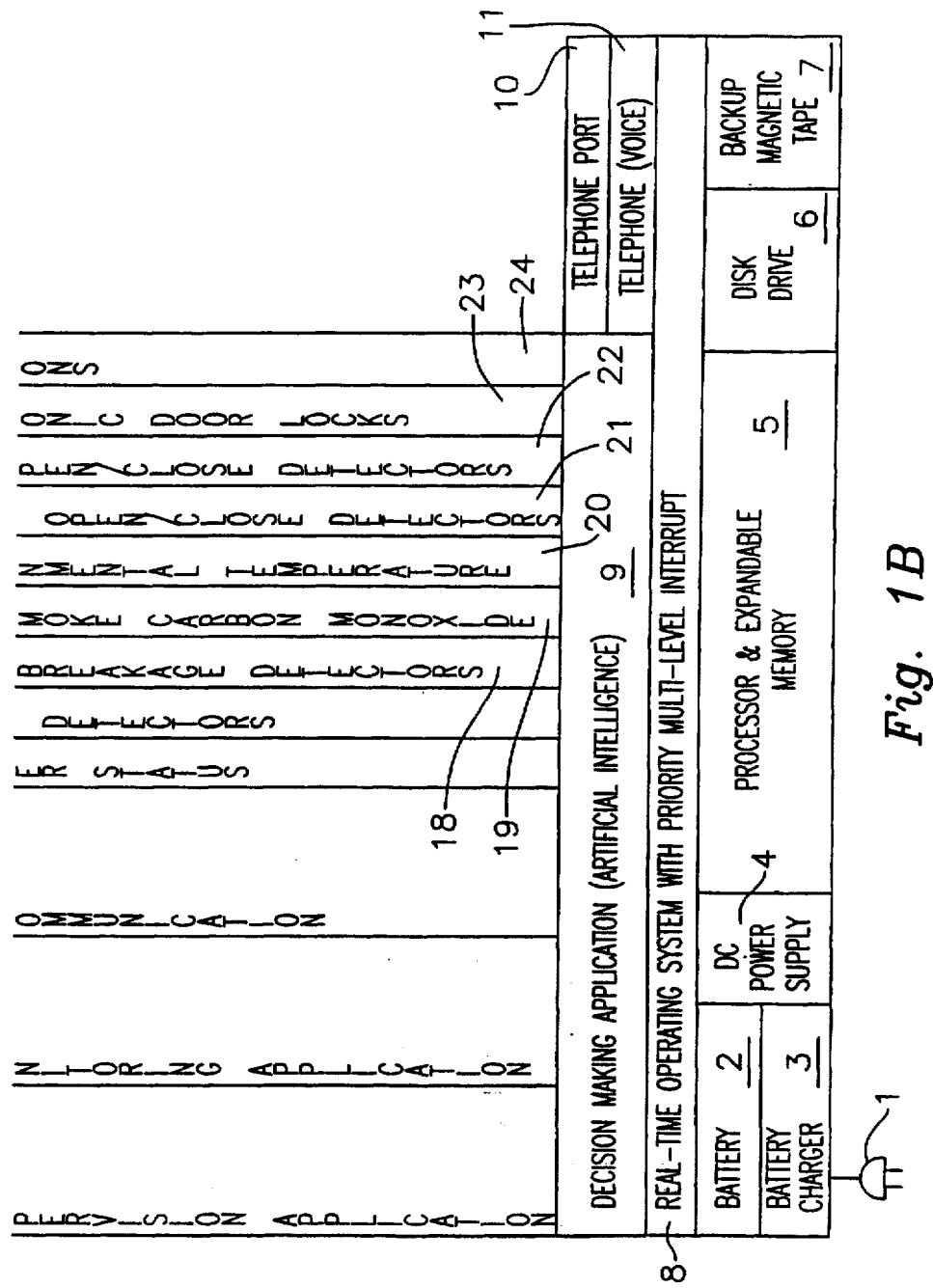
Figure 4A:
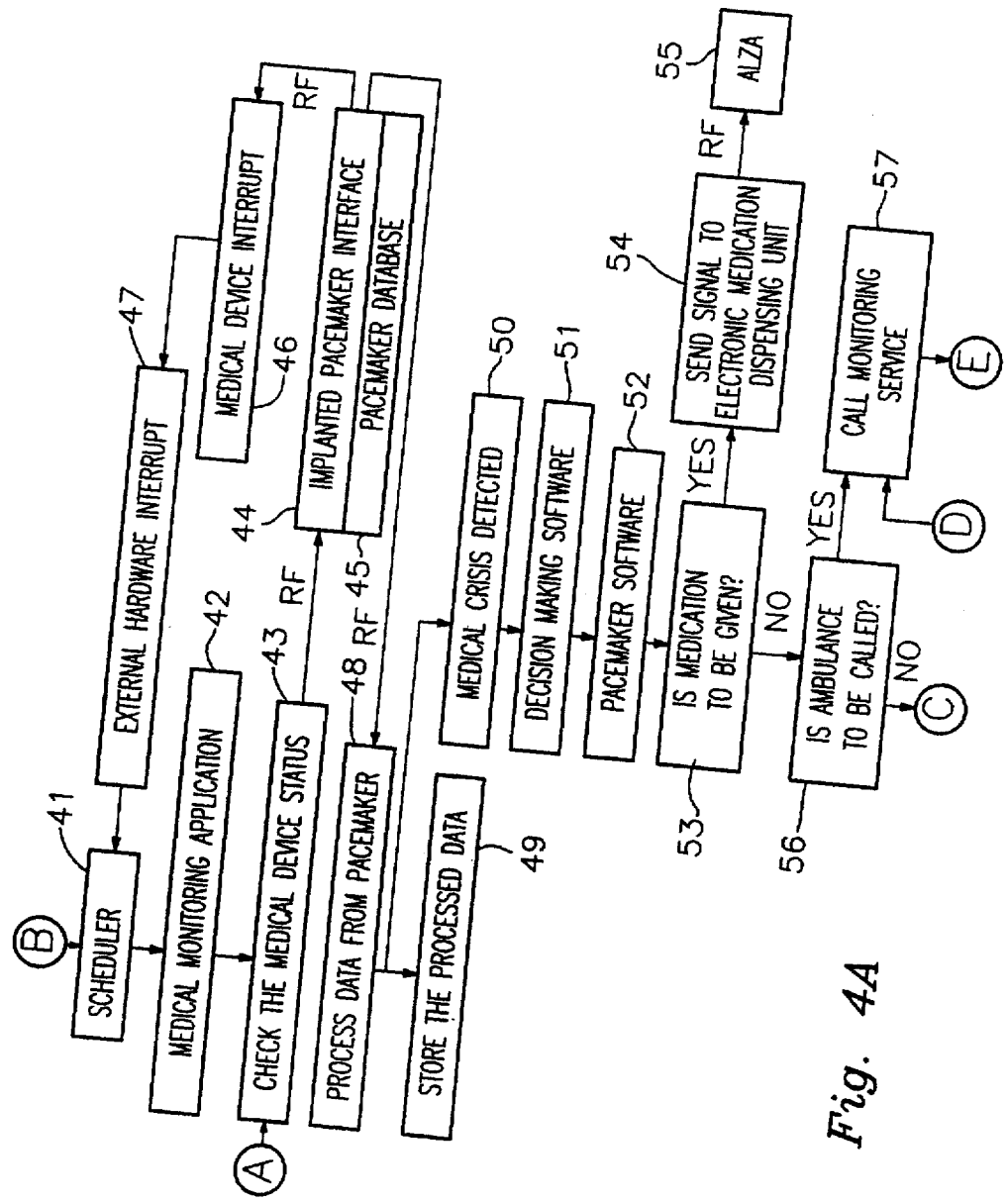
Figure 4B:
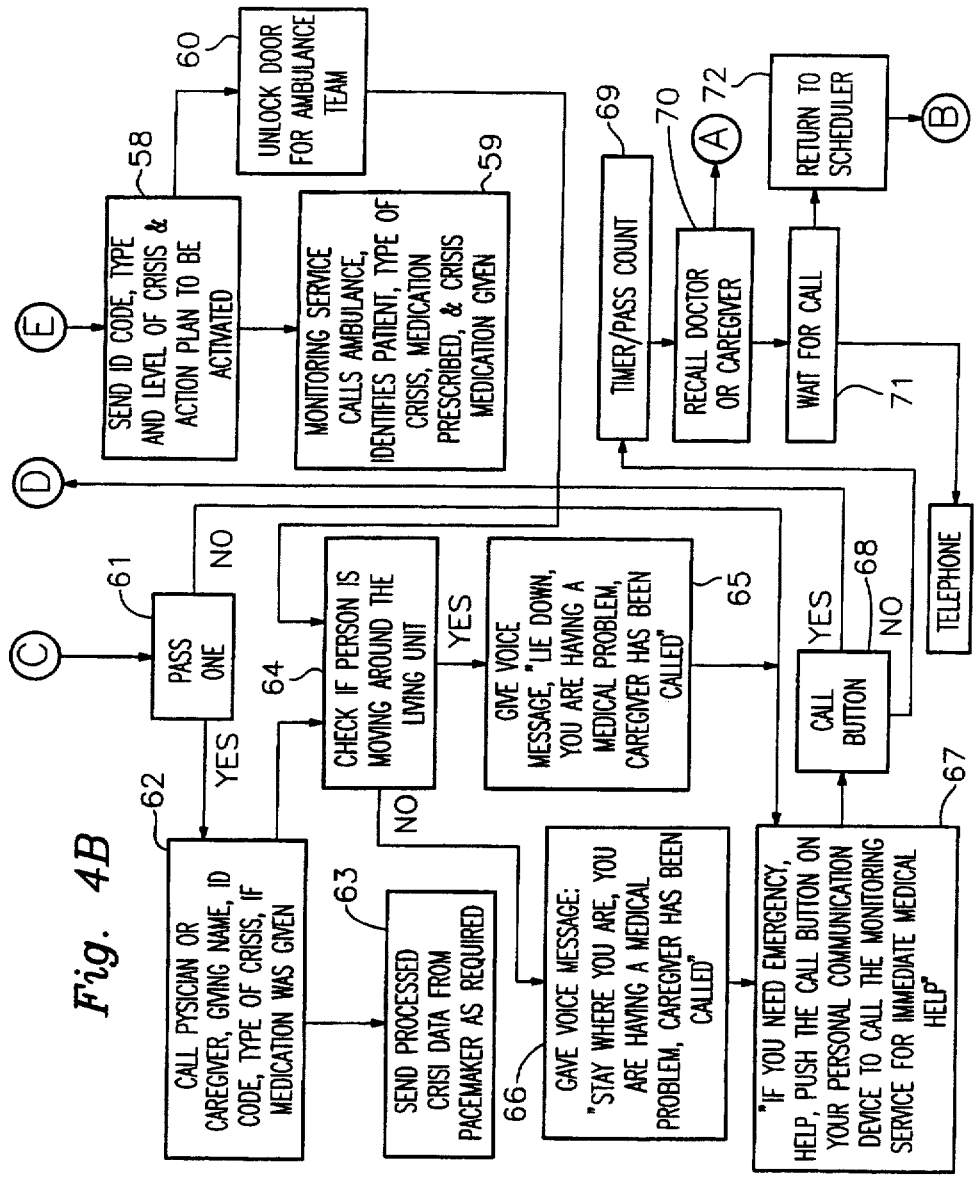

It is certified that error appears in the above-identified patent and that said Letters Patent is hereby corrected as shown below:

Drawing,
Cancel Figures 1B, 4A, and 4B and substitute the attached Figures 1B, 4A, and 4B; and cancel the lower portion of the drawing on the frontpiece of the patent and substitute therefor that shown in Figure 1B.

Signed and Sealed this

Second Day of April, 2002

Attest:

Attesting Officer

JAMES E. ROGAN
Director of the United States Patent and Trademark Office